(12) United States Patent
Kugler (10) Patent No.: US 11,197,976 B2
(45) Date of Patent: Dec. 14, 2021

(54) METHOD AND PROCESS TO PRODUCE A MEDICAL DEVICE

(71) Applicant: Advantech Plastics LLC, Woodstock, IL (US)

(72) Inventor: Gerald J. Kugler, Pingree Grove, IL (US)

(73) Assignee: Advantech Plastics LLC, Woodstock, IL (US)

( * ) Notice: Subject to any disclaimer, the term of this patent is extended or adjusted under 35 U.S.C. 154(b) by 222 days.

(21) Appl. No.: 16/381,704

(22) Filed: Apr. 11, 2019

(65) Prior Publication Data

US 2019/0314603 A1 Oct. 17, 2019

Related U.S. Application Data

(60) Provisional application No. 62/656,701, filed on Apr. 12, 2018.

(51) Int. Cl.
| | |
|---|---|
| *A61M 25/00* | (2006.01) |
| *B29C 45/17* | (2006.01) |
| *B29C 45/04* | (2006.01) |
| *A61B 1/00* | (2006.01) |
| *A61B 17/00* | (2006.01) |
| *B29C 45/14* | (2006.01) |
| *B29C 45/00* | (2006.01) |
| *B29C 45/06* | (2006.01) |

(52) U.S. Cl.
CPC ..... *A61M 25/0014* (2013.01); *B29C 45/0441* (2013.01); *B29C 45/1756* (2013.01); *A61B 1/0011* (2013.01); *A61B 2017/00526* (2013.01); *A61M 25/001* (2013.01); *A61M 25/0009* (2013.01); *A61M 25/0015* (2013.01); *A61M 25/0097* (2013.01); *B29C 45/06* (2013.01); *B29C 45/14598* (2013.01); *B29C 2045/0094* (2013.01)

(58) Field of Classification Search
CPC .......... A61M 25/0014; A61M 25/0009; A61M 25/001; A61M 25/0015; A61M 25/0097; A61B 1/0011; A61B 2017/00526; B29C 45/0441; B29C 45/1756; B29C 45/06; B29C 45/14598; B29C 2045/0094
USPC ........................................................ 425/190
See application file for complete search history.

(56) References Cited

U.S. PATENT DOCUMENTS

| | | | | |
|---|---|---|---|---|
| 6,192,568 | B1* | 2/2001 | Kafrawy | A61M 25/0009 264/157 |
| 2015/0051587 | A1* | 2/2015 | Rolsted | B29C 45/56 604/538 |
| 2016/0184551 | A1* | 6/2016 | Nyman | A61M 25/0068 604/544 |
| 2017/0151417 | A1* | 6/2017 | Takemura | B29C 45/72 |
| 2019/0275294 | A1* | 9/2019 | Trosken | A61M 25/0045 |

FOREIGN PATENT DOCUMENTS

EP 3536371 A1 * 9/2019 ........ A61M 25/0045

* cited by examiner

*Primary Examiner* — Joseph S Del Sole
*Assistant Examiner* — Lawrence D. Hohenbrink, Jr.
(74) *Attorney, Agent, or Firm* — Vidas, Arrett & Steinkraus, PA; Richard A. Arrett; Edwin E. Voigt, II (57) ABSTRACT

The inventive method for making a medical device includes providing a micro plastic tube; molding a hub onto the tube; trimming the tube to a predetermined length; molding a tip onto the tube, and creating a tip that contains a micro orifice at a predetermined angle.

12 Claims, 10 Drawing Sheets

METHOD AND PROCESS TO PRODUCE A MEDICAL DEVICE

CROSS-REFERENCE TO RELATED APPLICATIONS

This application claims the benefit of and priority to U.S. Provisional Application No. 62/656,701, filed Apr. 12, 2018, the entire contents of which are herein incorporated by reference.

STATEMENT REGARDING FEDERALLY SPONSORED RESEARCH

Not Applicable

FIELD OF THE INVENTION

The invention relates to a method and apparatus for making a medical device, and more specifically a method of molding a hub directly to a micro plastic tube and molding a tip containing a micro orifice at a specified angle directly to the micro plastic tube.

BACKGROUND OF THE INVENTION

Manufacturing a medical device using a micro plastic tube can be very difficult. It can be difficult to mold a hub onto the plastic tube, especially so that the plastic tube is adequately retained in the hub after molding without causing blow out, pull out or fall out. It can also be difficult to mold a tip onto the plastic tube without causing any obstructions or partial blockages for liquid flow out of the orifice end f the plastic tube.

BRIEF SUMMARY OF THE INVENTION

This medical device serves as a delivery system for administering liquid medications in humans and animals. Applicant has developed methods and processes to enhance the manufacturing and performance of the device. These developments relate to the manufacturing methods and processes required to achieve critical requirements for the functionality of the device. Specifically they relate to the fluid flow characteristics and mechanical aspects of the device to ensure reliable performance.

The inventive method for making a medical device includes providing a micro plastic tube; molding a hub onto the tube; trimming the tube to a predetermined length; molding a tip onto the tube, and creating a tip that contains a micro orifice at a predetermined angle.

The predetermined angle can be 45 degrees. The micro orifice at the tip can be between 0.008 to 0.012 inches in diameter. The plastic tube has a thin wall of approximately 0.003 inches thick. The plastic tube can be made of PEBAX and the hub can be made of polycarbonate.

The micro orifice is created using a conically shaped orifice pin. The apparatus used to make the medical device is created using a shuttle mold system and a vertical injection molding machine. The shuttle mold system has one top section and two bottom sections. The shuttle mold system is mounted in a vertical injection molding machine with the two bottom sections mounted 180 degrees from each other on a rotating table and the top section mounted in a fixed position above the rotating table. After molding, the table rotates 180 degrees for removal of parts and inserting fixtures for the next device manufacture cycle.

DETAILED DESCRIPTION OF THE INVENTION

While this invention may be embodied in many forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The method for manufacturing this product consists of a shuttle mold system and vertical injection molding machine. The shuttle mold system has one top section and two bottom sections. The shuttle mold system is mounted in a vertical injection molding machine. The two bottom sections are mounted 180 degrees from each other on a rotating table and the top section is mounted in a fixed position above the rotating table. The two bottom sections move as the table rotates 180 degrees and align with the one top section during molding. After molding the table rotates 180 degrees for removal of parts and inserting of fixtures for the next cycle. The bottom sections are accessible to the operator at the front of the machine during each index for inserting and removing fixtures and components. The process requires a highly skilled operator to perform all necessary functions such as: preparing the fixtures, loading fixtures, ensuring sub-assemblies are positioned properly, and removing parts and fixtures. This is a continuous process that requires operator interaction for the molding operations.

Figure 1:
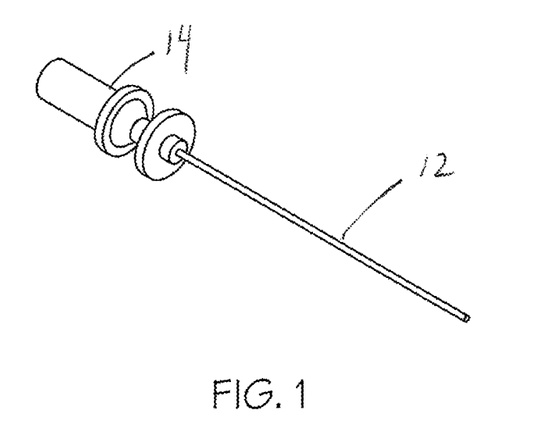
FIG. 1 is a view of a micro plastic tube molded to a plastic housing.
Figure 2:
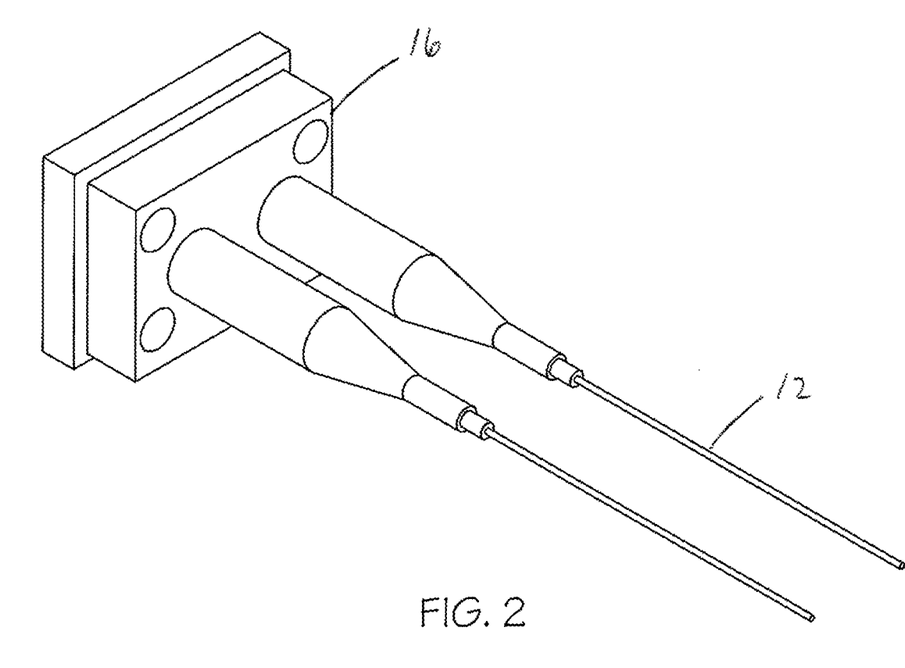
FIG. 2 is a view of the tooling fixture with the tube installed on a tooling fixture pin to be placed in a mold for over molding the hub onto the tube.
Figure 3:
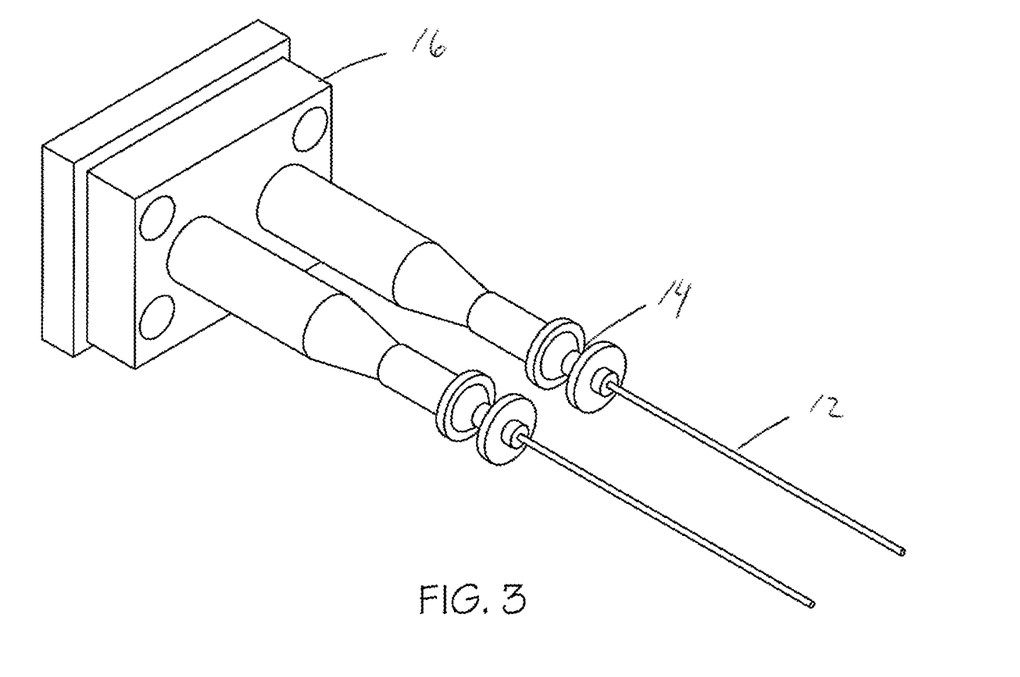
FIG. 3 is a view showing the tooling fixture after over molding the hub into the micro plastic tube.

The method for manufacturing this product consists of two stages. In stage 1 the micro plastic tube 12 is molded to a plastic housing 14 as shown in (FIG. 1). First, the micro plastic tube 12 is placed on a tooling fixture 16 consisting of a pin (not shown because under the plastic tube) that matches the inside diameter of the tube (FIG. 2). The fixture 16 containing the tube 12 is placed in a mold and the hub 14 is over molded on the tube 12 (FIG. 3). In effect the tube 12 and fixture 16 acts as an insert for over molding the hub 14.

Figure 4:
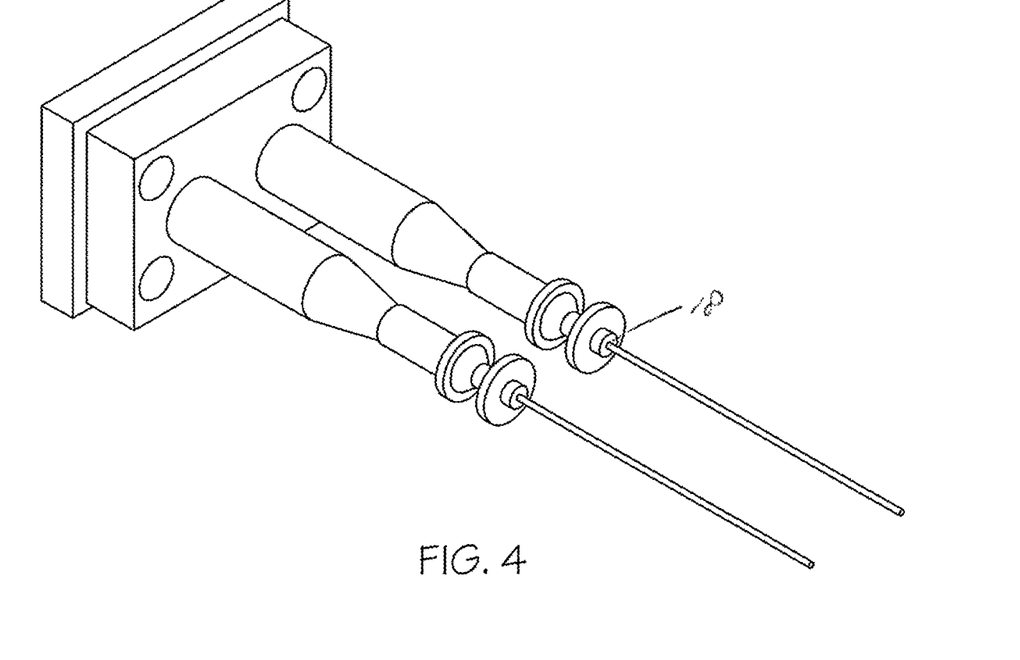
FIG. 4 is a view showing the interface between the tube and the hub.

This process is critical because it determines the retention of the tube 12 to the hub 14 while maintaining the integrity of the inside diameter of the micro plastic tube 12 during molding (FIG. 4) which is critical for the proper performance of the product in the end use application. The flow through the tube 12 cannot be obstructed by excess material, flash, debris, etc. The specific configuration of the tooling fixture and set up in the mold minimizes this occurrence.

FIG. 2 shows the tooling fixture 16 with tube 12 installed on tooling fixture pin (inside tube 12) to be placed in mold for over molding the hub 14.

FIG. 3 shows the tooling fixture 16 after over molding the hub 14 on the micro tube 12. The tube to hub interface 18 (seen best in FIG. 4) is critical to obtain adequate tube 12 retention to the hub 14 without jeopardizing the integrity of the opening in the tube during over molding. This is accomplished by ensuring that the exact location of the plastic tube is maintained on the fixture 16 during the process of over molding the hub 14, and ensuring the fixture set up in the mold is precisely maintained.

Figure 5:
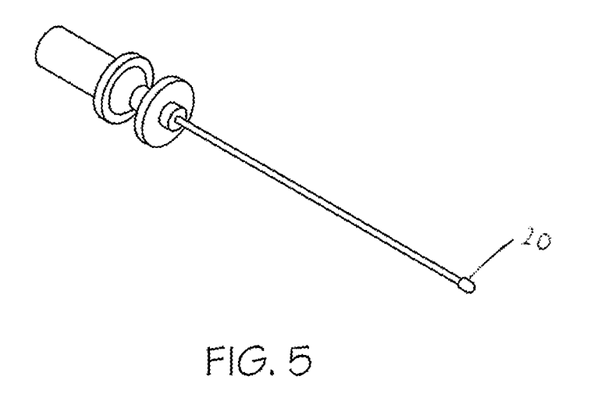
FIG. 5 is a view showing the tip over molded onto the plastic tube.

The second stage is over molding a tip 20 containing a micro orifice 22 (0.008"-0.012") at a specified angle on the micro plastic tube 12. The sub-assembly from the first step is placed on a tooling fixture 24 (see FIG. 7A) consisting of a pin 26 that matches the inside diameter of the tube 12. The fixture 24 is placed in a mold and the tip 20 is over molded on the micro plastic tube 12 (FIG. 5). The tube 12 and hub 14 with tooling fixture 24 act as an insert for over molding of the tip 20. This method is critical because it creates the molded tip 20 on the end of the plastic tube that contains a micro orifice 22 at a 45 degree angle (or any desired angle). In addition the tip 20 must be adequately attached to the tube 12 to maintain retention without causing any obstructions or partial blockages for liquid flow. The configuration of the tooling and molding process prevent this from occurring.

Figure 6:
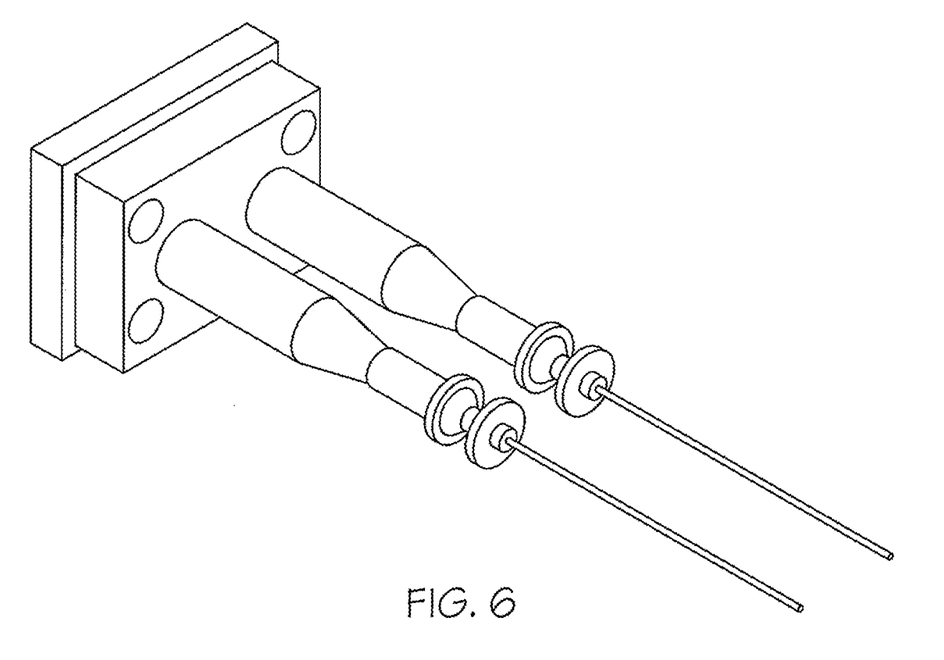
FIG. 6 is a view showing the tube trimmed to a specified length.

FIG. 6 shows the tube after being trimmed to a predetermined length. The hub 14 and micro tube 12 assembly requires a specific length of tube for successful over molding of the tip on the end of the micro tube. The tube length is determined by precisely placing the assembly on a calibrated fixture and trimming the tube to a specific length prior to over molding the tip. The tube is trimmed to fit the pin or mandrel used in the molding process and can therefore be any desired length.

Figure 7A:
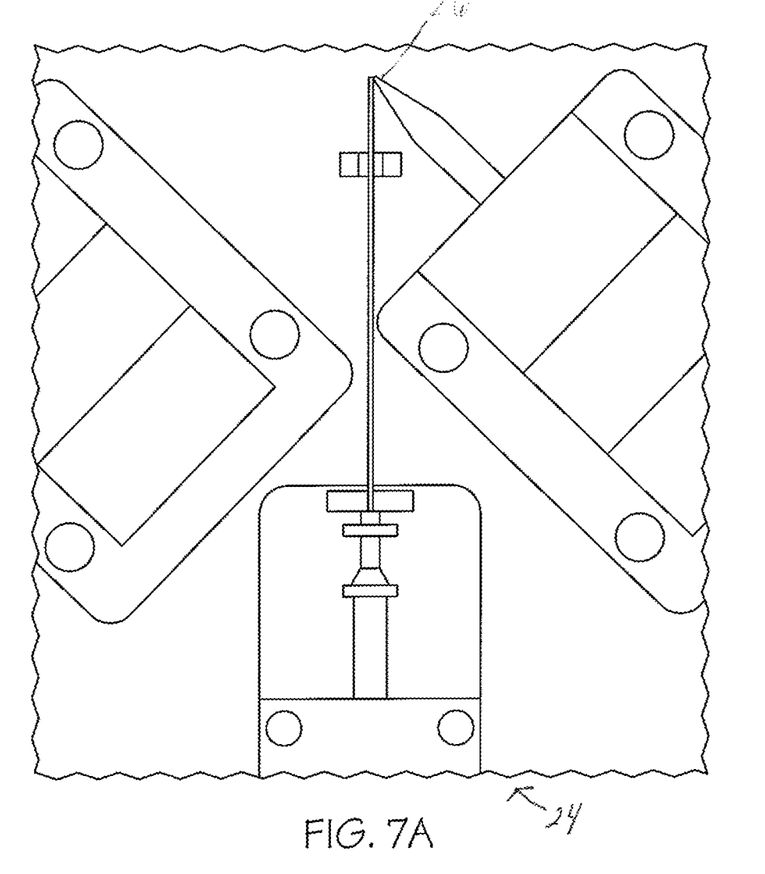
FIGS. 7A and 7B is a view showing the trimmed tube placed on another fixture and positioned in the mold.
Figure 7B:
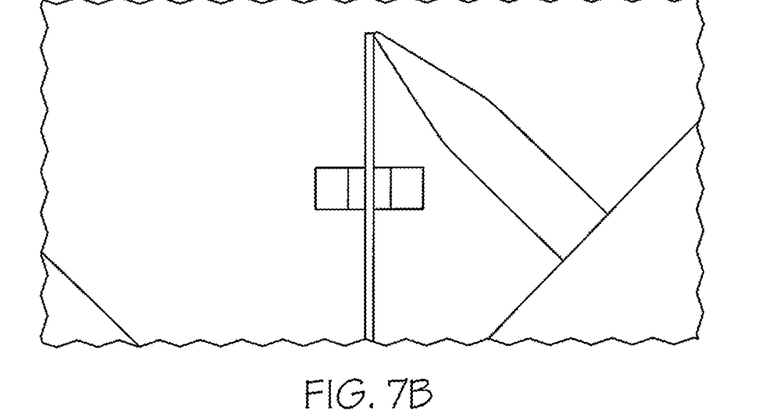

FIGS. 7A and 7B shows the fixture, shown generally at 24, which is used once the hub and tube assembly is trimmed to proper length and is ready for over molding the tip 20 on the micro tube 12. The assembly is placed on fixture 24 and positioned in the mold.

Figure 8:
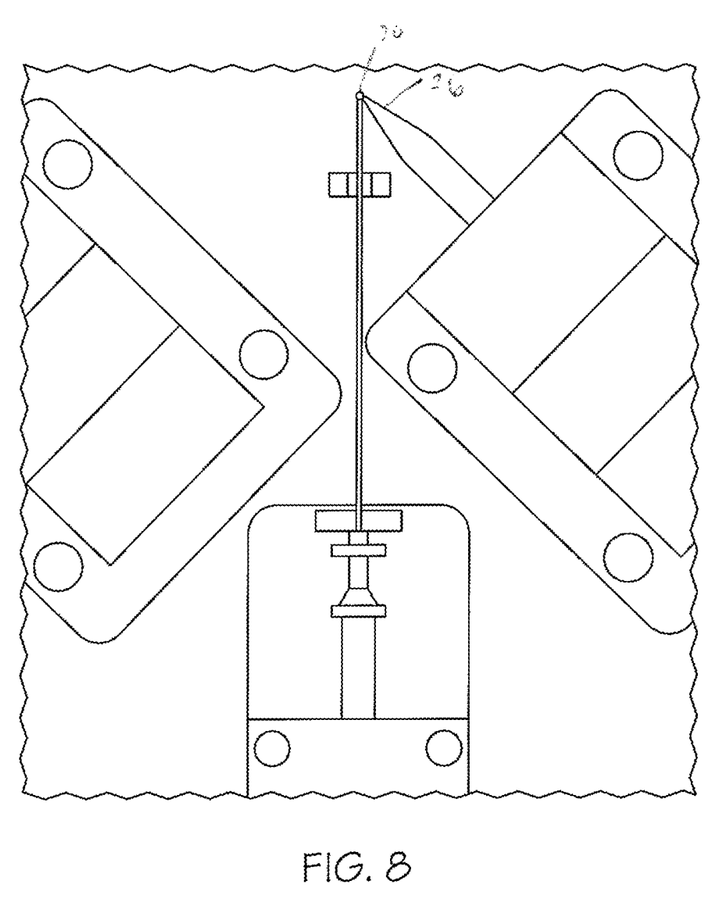
FIG. 8 is a view showing the special pin which produced the micro orifice in the over molded tip.

FIG. 8 shows the special pin 26 used to produce the micro orifice 22 in the tip 20 during the molding. FIG. 8 shows the fixture configured to produce a micro orifice 22 in the tip 20 during over molding.

Figure 9A:
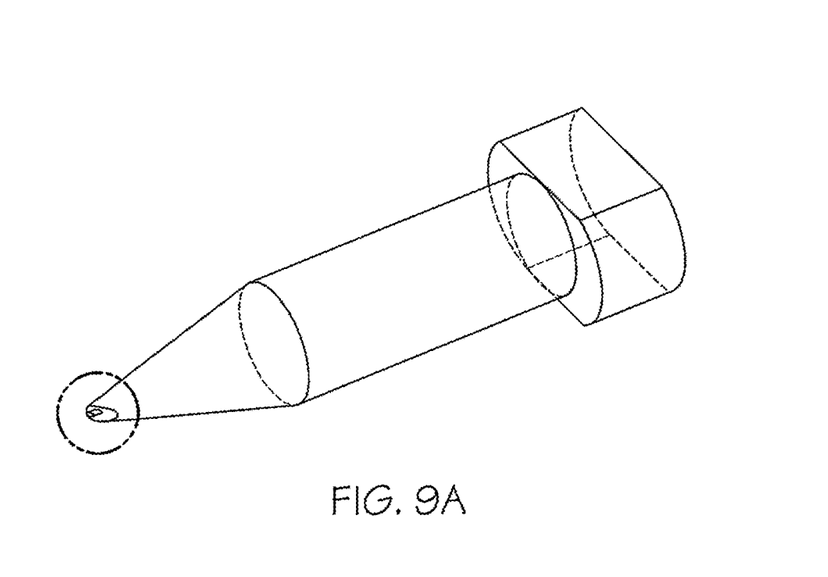
FIGS. 9A and 9B show the pin and an enlarged view of the end of the pin.
Figure 9B:
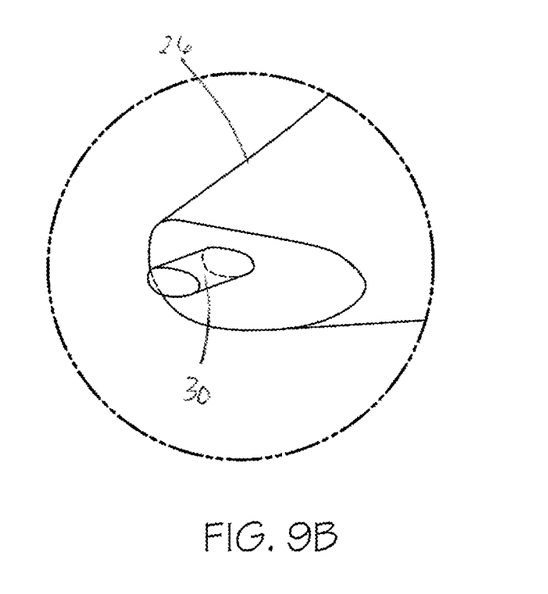
Figure 10A:
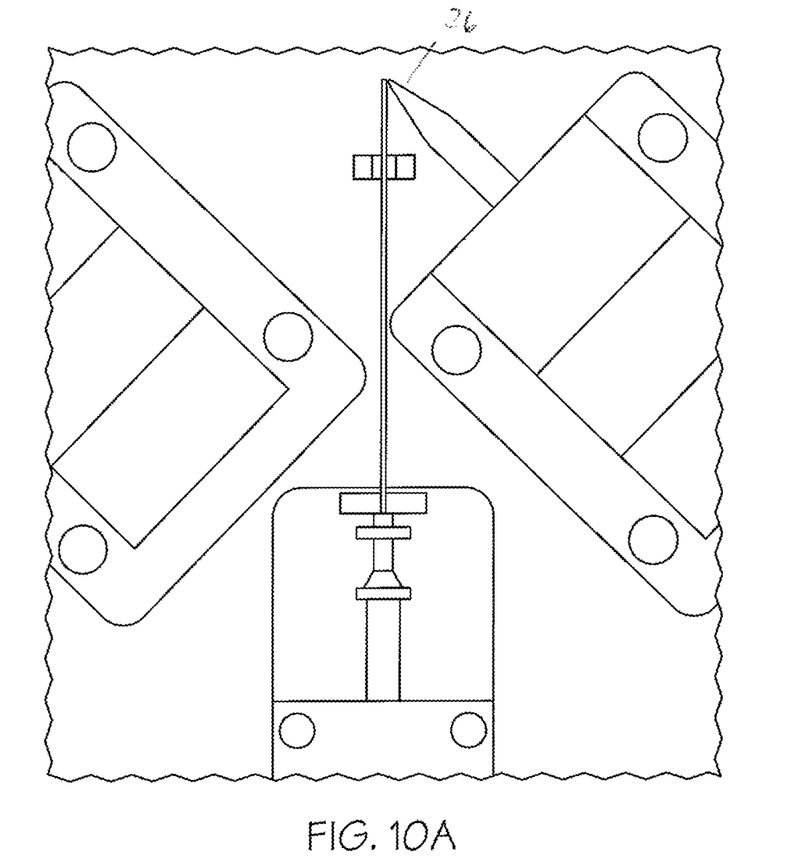
FIGS. 10A and 10B show the tooling for making the tip and an enlarged view of the pin positioned to make the tip.
Figure 10B:
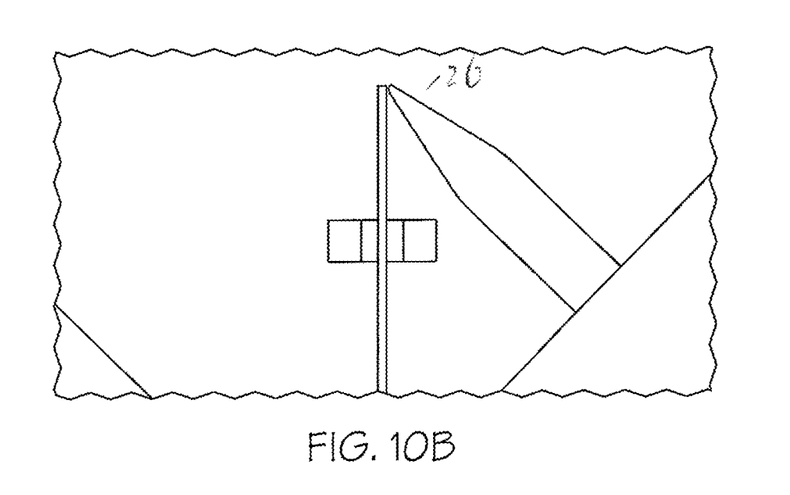
Figure 11:
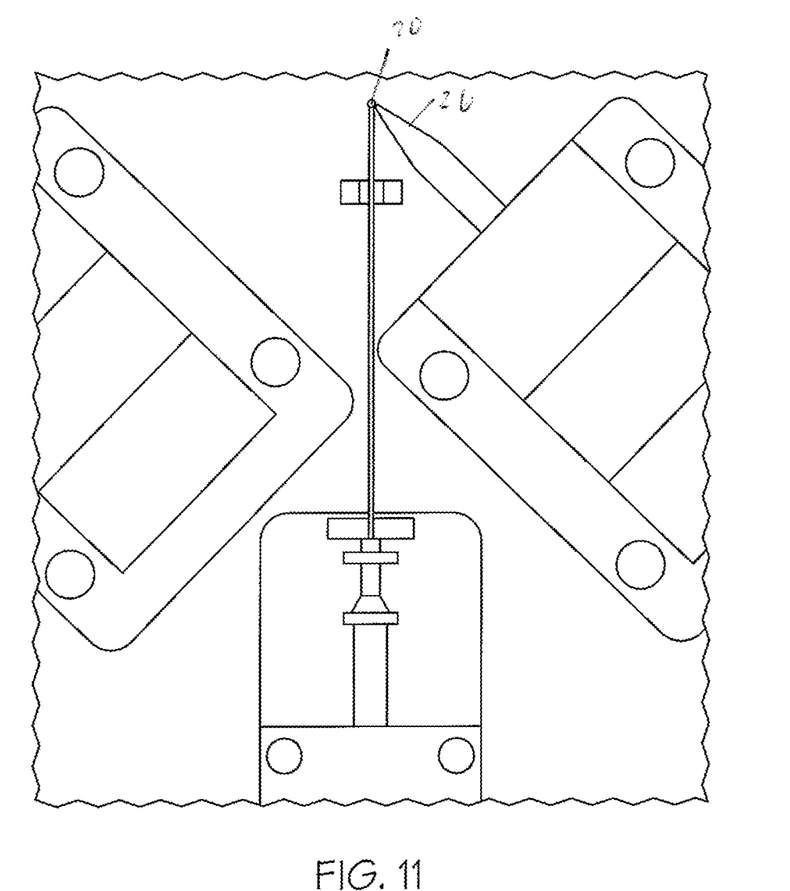
FIG. 11 shows the over molded tip on the end of micro tube.
Figure 12:
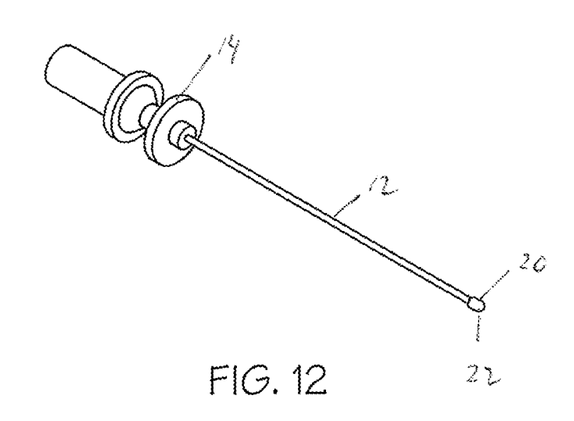
FIG. 12 shows the tip and the orifice in the tip which is placed at a 45 degree angle.

FIGS. 9A and 9B show an example micro orifice of 0.010 inches over molded into tip 20, with the orifice 22 placed at a 45 degree angle. The conically shaped tip of pin 26 has a 0.010 inch diameter pin 30 which creates the micro orifice. FIGS. 10A and 10B also show this step in further detail. FIG. 11 shows the tip 20 produced by pin 26. FIG. 12 shows the tip 20 is over molded to tube 12 in such a way that retention is maintained without obstructions in the micro orifice 22.

Figure 13A:
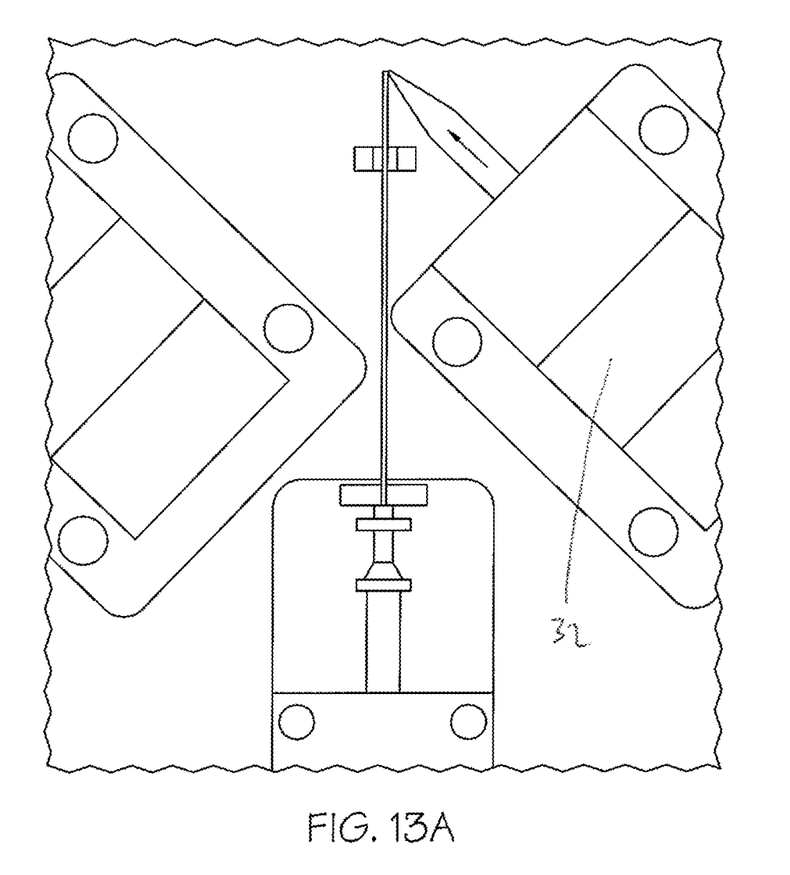
FIGS. 13A and 13B show the slide holding the pin in the forward position and the back positions.
Figure 13B:
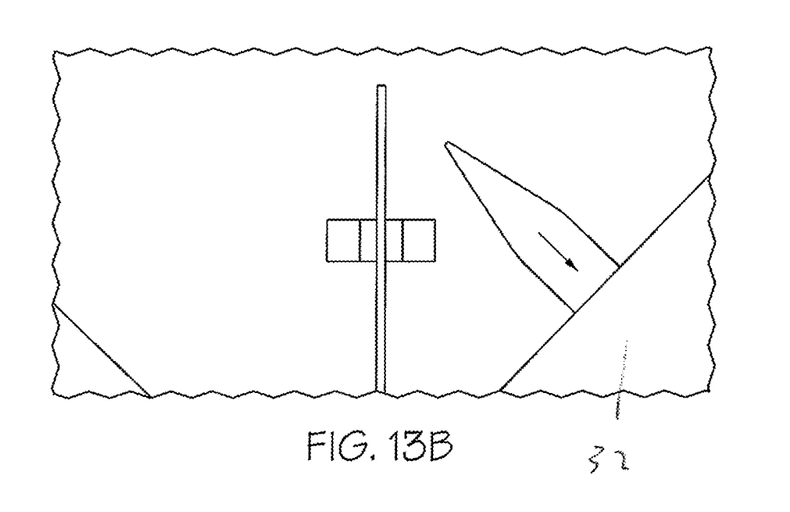

FIGS. 13A and 13B shows the tooling configuration for over molding tip 20 on micro tube 12. FIG. 13B shows the slide 32 in the back position and FIG. 13A shows the slide 32 in the forward position. The slide 32 with special pin 26 "shuts off" against the pin that is part of the hub and tube assembly fixture.

What is claimed is:

1. A method of making a medical device for delivering liquid medications in humans and animals, comprising the steps of:
   providing a micro plastic tube having a hub end and an orifice end;
   molding a hub onto the hub end of the micro plastic tube;
   trimming the micro plastic tube to a predetermined length;
   molding a tip onto the orifice end of the micro plastic tube, and
   creating a micro orifice in the tip using a pin, which through the orifice the liquid medications are delivered, the orifice being constructed and arranged at a predetermined degree angle, relative to the tube.

2. The method of claim 1 wherein the predetermined angle is 45 degrees.

3. The method of claim 1 wherein the micro orifice is between 0.008 to 0.012 inches in diameter.

4. The method of claim 1 wherein the plastic tube has a thin wall of about 0.003 inches.

5. The method of claim 1 wherein the plastic tube inner diameter is not affected by molding the hub onto the tube, so that the plastic tube is adequately retained in the hub after molding to prevent blow out, pull out or fall out.

6. The method of claim 1 wherein the plastic tube is made of PEBAX.

7. The method of claim 1 wherein the hub is made of polycarbonate.

8. The method of claim 1 wherein the micro orifice is created using a conically shaped orifice pin.

9. The method of claim 1 wherein the medical device is created using a shuttle mold system and a vertical injection molding machine.

10. The method of claim 9 wherein the shuttle mold system has one top section and two bottom sections.

11. The method of claim 10 wherein the shuttle mold system is mounted in the vertical injection molding machine with the two bottom sections mounted 180 degrees from each other on a rotating table and the top section mounted in a fixed position above the rotating table.

12. The method of claim 11 wherein after molding, the table rotates 180 degrees for removal of parts and inserting fixtures for the next cycle.

* * * * *